United States Patent
Hofmann et al.

(10) Patent No.: US 7,998,463 B2
(45) Date of Patent: *Aug. 16, 2011

(54) TARGETED DELIVERY OF LIDOCAINE AND OTHER LOCAL ANESTHETICS AND A METHOD FOR TREATMENT OF COUGH, ASTHMA AND TUSSIVE ATTACKS

(75) Inventors: Thomas Hofmann, Doylestown, PA (US); Alan Bruce Montgomery, Medina, WA (US); Kevin Stapleton, Seattle, WA (US)

(73) Assignee: Gilead Sciences, Inc., Seattle, WA (US)

( * ) Notice: Subject to any disclaimer, the term of this patent is extended or adjusted under 35 U.S.C. 154(b) by 371 days.

This patent is subject to a terminal disclaimer.

(21) Appl. No.: 12/208,219

(22) Filed: Sep. 10, 2008

(65) Prior Publication Data

US 2009/0041676 A1 Feb. 12, 2009

Related U.S. Application Data

(62) Division of application No. 11/045,226, filed on Jan. 28, 2005, now Pat. No. 7,452,523.

(60) Provisional application No. 60/635,022, filed on Dec. 9, 2004, provisional application No. 60/611,656, filed on Sep. 20, 2004, provisional application No. 60/539,836, filed on Jan. 27, 2004.

(51) Int. Cl.
*A61K 9/00* (2006.01)
*A61K 9/12* (2006.01)
*A61K 9/14* (2006.01)

(52) U.S. Cl. ............... 424/45; 424/46; 424/43; 424/434

(58) Field of Classification Search .................. 424/45, 424/46, 43, 434
See application file for complete search history.

(56) References Cited

U.S. PATENT DOCUMENTS

| | | | |
|---|---|---|---|
| 2003/0171402 A1 | 9/2003 | Gleich et al. | |
| 2003/0232019 A1* | 12/2003 | Basu et al. | 424/46 |
| 2009/0004279 A1* | 1/2009 | Hofmann et al. | 424/489 |

OTHER PUBLICATIONS

Emmanuel Udezue, Lidocaine inhalation for Cough Suppression, Clinical Notes, pp. 206-207, Oct. 2000.*
M. L. Decco, et al., Nebulized Lidocaine in the Treatment of Severe Asthma in Children: a Pilot Study, *Annals of Allergy, Asthma & Immunology*, V.82, No. 1, Jan. 1, 1999, Arlington Heights, IL, USA.
Loren W. Hunt, et al. Effect of Nebulized Lidocaine on Severe Glucocorticoid-Dependent Asthma, *Mayo Clin Proc*, 71:361-368 (1996).
PARI's eFlow(R), an Electronic Aerosol Device for Medication Delivery, Receives FDA 510(k) Market Clearance, *PARI Serosol Research Institute*, pp. 1-2; May 18, 2004, Monterey, California, USA.
European Supplemental Search Report, European Patent Office, Dec. 16, 2009.
Abuan, Tammy B.S.N., Inhaled Lidocaine for the Treatment of Asthma: Lack of Efficacy in Two Double-Blind, Randomized, Placebo-Controlled Clinical Studies, Journal of Aerosol Medicine and Pulmonary Drug Delivery, vol. 23/6, pp. 381-388, 2010.
Iacono, Aldo T., et al., Dose-Related Reversal of Acute Lung Rejection by Aerosolized Cyclosporine, Am J Respir CrIt Care Med, vol. 155, pp. 1690-1698, (1997).
Poulton, Thomas J., M.D., et al., Cough suppression by Lidocaine, Anesthesiology, vol. 50/5, pp. 470-472, May 1979.
Sanders, Robert F., et al., Prolonged Suppression of Cough After Inhalation of Lidocaine in a Patient With Sarcoid, JAMA, vol. 252/17; pp. 2456-2457, Nov. 2, 1984.
Sherman, James M., Breaking the Cycle: Lidocaine Therapy for Habit Cough, J. Florida M.A., vol. 84/5, pp. 308-309, Jun./Jul. 1997.
Trochtenberg, S., Nebulized lidocaine in the treatment of refractory cough, Chest, 105:1592-1593, 1994.

* cited by examiner

*Primary Examiner* — Mina Haghighatian
(74) *Attorney, Agent, or Firm* — Peters Verny, LLP

(57) ABSTRACT

An anti-tussive nebulized solution for targeted delivery of lidocaine into conducting and central airways. A method for treatment of cough and tussive attacks or episodes using said lidocaine solution. A nebulized lidocaine solution administered in daily dose from about 10 mg to 80 mg of lidocaine dissolved in a saline and nebulized into an aerosol having a mass median aerodynamic diameter 3 μm to 10 μm and a geometric standard deviation less than 1.7 using an electronic nebulizer.

13 Claims, 1 Drawing Sheet

TARGETED DELIVERY OF LIDOCAINE AND OTHER LOCAL ANESTHETICS AND A METHOD FOR TREATMENT OF COUGH, ASTHMA AND TUSSIVE ATTACKS

This application is based on and claims priority of the Provisional application Ser. No. 60/635,022, filed on Dec. 9, 2004, Ser. No. 60/611,656 filed on Sep. 20, 2004, and Ser. No. 60/539,836 filed on Jan. 27, 2004.

BACKGROUND OF THE INVENTION

1. Field of the Invention

The current invention concerns generally a method for targeted delivery of local anesthetics for treatment of cough and tussive attacks and episodes. In one aspect, the invention concerns an improved anti-tussive solution for targeted delivery of a local anesthetic to lungs by nebulization. In particular, the invention concerns an improved anti-tussive lidocaine solution for targeted delivery of lidocaine into conducting and central airways as well as a method using said lidocaine solution for treatment of cough and tussive attacks or episodes.

The solution for inhalation comprising lidocaine or another local anesthetic is administered in daily dose from about 10 mg to 160 mg. Lidocaine or another anesthetic dissolved in a normal or diluted saline is nebulized into an aerosol having a mass median aerodynamic diameter (MMAD) within a range of 3 μm to 10 μm using an electronic nebulizer able to generate a substantially monodisperse particle spectrum. The solution comprising lidocaine or any other anesthetic nebulized according to the invention described herein is deposited predominantly in the target area for cough receptors, namely in the upper, conducting, and central airways, without any substantial residue of the anesthetic found in the oropharyngeal area or in the lower lungs.

In alternative, the local anesthetic solution suitable for treatment of cough may be administered nasally, orally or intravenously when appropriately formulated for such use.

For nasal administration, the local anesthetic is formulated as drops comprising about 2.5 mg of the drug in 0.3 ml of solvent. For oral administration, 50-100 mg of the drug is administered orally once or twice daily. For intravenous administration, the daily dose is up to 2000 mg administered once or several times a day.

The method for treatment of cough, asthma and tussive asthmatic attack is safer than the treatments described previously in that the secondary undesirable symptoms such as bronchospasm, loss of gag reflex and numbing of a pharyngeal region due to anesthetic properties of lidocaine or another anesthetic compound are prevented. The method is also more efficacious because it permits use of a lesser amount of lidocaine when the solution is nebulized using electronic nebulizer and delivers this solution in shorter time. Additionally, the electronic nebulizers produce a substantially monodisperse spectrum of particles substantially within a range of 3 μm to 10 μm of which a large percentage is deposited in the central airways.

BACKGROUND AND RELATED DISCLOSURES

Cough is a natural response to mechanical and chemical irritation of trachea and bronchi. The physiological role of cough is to prevent aspiration of foreign objects or excess secretion within the respiratory tract and to remove such objects or secretion or exudates from the trachea and bronchi.

Cough is a very common problem in medical practice as it accompanies a great variety of viral or bacterial infections including pneumonia, cold or flu, or underlying diseases, such as asthma, emphysema, lung cancers, etc.

While there are several anti-tussive agents available on the market, most of these agents cause secondary undesirable symptoms, such as drowsiness, tiredness and some of these agents, such as for example codeine, are also addictive.

It would therefore be advantageous to have available a method for controlling cough which would have no such undesirable secondary symptoms.

In recent years, use of lidocaine was proposed as a supplemental treatment for suppression of cough and as pretreatment in instances where respiratory examination such bronchoscopy or X-rays could be affected by a patient's cough.

U.S. Pat. No. 6,362,197B1, for example, describes compositions possessing anti-tussive activity administered by nebulization using an ultrasonic, meter-dose inhaler, jet nebulizer and dry powder inhaler. As a pretreatment of testing a new anti-tussive quaternary ammonium compound in guinea pigs exposed to citric acid or capsaicin, lidocaine aerosol was generated using the UltraVilbis ultrasonic nebulizer (0.15 ml/min) and administered in dosages 0.1, 1, and 10 mg/ml. This pretreatment was shown to postpone a first cough at concentrations of 0.1 and 10 mg/ml, but not at 1 mg/ml and to significantly decrease a number of coughs at 10 mg/ml concentration.

*JAOA,* 98 (No 3): 170-172 (1998) describes the treatment of a patient suffering from a persistent refractory tussive syncope. The patient was unsuccessfully treated with a large number of anti-tussive drugs. Consequently, and in conjunction with these other drugs, the patient was treated with 1 ml of 1% nebulized lidocaine every 4 hours for 10 days. Such combination treatment of lidocaine with other anti-tussive drugs administered by nebulization or intravenously was able to resolve syncopal episodes.

*Chest,* 105:1592-93 (1994) describes treatment of chronic refractory cough with acetaminophen and codeine supplemented with 3 ml of 1% nebulized lidocaine twice a day for 6-10 weeks. The combination of nebulized lidocaine with other drugs was effective for treatment of refractory cough.

*JAMA,* 252 (No 17) 2456-2457 (1984) describes extended suppression of cough with inhaled 10 ml of 4% (40 mg) lidocaine administered by DeVilbiss nebulizer at a flow rate of 6 L/min for approximately 30 minutes. Under these conditions, after the first treatment cough was suppressed for about 9 weeks and for 7.5 weeks after the second administration. However, during this regimen, a substantial anesthesia of oropharynx was observed.

*J. Canadian Assoc. Radiol.,* 22: 199-200 (1971) reference generically describes the use of local anesthetics as a pretreatment for bronchography. Local anesthetics are administered to the tip of the tongue prior to the procedure at a maximum effective concentration, determined for lidocaine to be 4%.

*Am. J. Emerg. Med.,* 19:206-207 (2001) discloses lidocaine inhalation for cough suppression preceded by inhalation of nebulized albuterol. The lidocaine (1 ml of 1%) solution was diluted in 4 ml of saline to give 0.25% solution with oxygen 4-6 L/min delivered until nebulization was complete. Subsequently, 2 ml of the 1% solution was administered every 4-6 hours. Nebulization was preceded by delivery of 1 ml of albuterol and could be repeated every 4-6 hours, with even more concentrated solution (up to 4%). The reference further discloses that administration of lidocaine triggers bronchospasm requiring, as a pretreatment, administration of 5 mg of nebulized albuterol and/or 0.5 mg of budesonide. The doses of lidocaine were 10 to 20 mg every 4-6 hours up to 40-120 mg per day. Under these conditions, inhalation of lidocaine abolished cough but not bronchoconstriction.

*Regional Anesthetics*, 18:312-314 (1993) describes a treatment of persistent cough after stellate ganglion block. Treatment was achieved with nebulized lidocaine (1 ml of 2%) in 2 ml of normal saline solution administered at the same time as the oxygen mask.

*British J. Pharmacol.*, 138:407-416 (2003) describes a novel antitussive agent, RSD931, and compared its activity to that of nebulized lidocaine in guinea pigs. The drugs were nebulized using an ultrasonic DeVilbis Ultraneb 2000 nebulizer and administered in amounts from 0.1 to 10 mg/ml. Lidocaine pretreatment had no significant effect on the time course of cough responses when administered as aerosol solution in these concentrations but did appear to delay onset of the first cough and reduce the total number of coughs. When used in from 10 to 30 mg/ml concentration, lidocaine pretreatment reduced the total number of coughs induced by capsaicin.

*J. Appl. Physiol.*, 74: 1419-1424 (1993) describes the effect of nebulized lidocaine on ventilatory response to $CO_2$ in healthy subjects. In this study, 10 ml of 4% lidocaine was nebulized with a Pulmosonic ultrasonic nebulizer or with a Wright jet nebulizer for 20 minutes. Particle size distribution and nebulizer output were determined. For Pulmosonic nebulizer, MMAD for lidocaine was 5.28 μm at nebulizer output of 0.16 g/min whereas for Wright nebulizer the MMAD for lidocaine was 1.76 at 0.25 g/min. This reference clearly shows that the ventilatory response to $CO_2$ changes when administered by different nebulizers.

*Am. Rev. Respir. Dis.*, 122:823-828 (1980) described effect of inhaled lidocaine on the ventilatory and airway responses using 4% lidocaine aerosol in patients with bronchial asthma. Lidocaine solution was aerosolized using a Vaponephrine nebulizer at a flow rate 5L/min. Particle size was 5.6 μm, with time delivery between 10 and 15 minutes.

*Br. J. Anaest.*, 54:853-856 (1982) describes the use of lignocaine for suppression of coughing. Lignocaine was administered (2 ml of 2%) before fibreoptic bronchoscopy. The reference discloses that when nebulized lignocaine is used as an antitussive agent before fibreoptic bronchoscopy, it suppresses cough within 10-15 minutes.

*Thorax*, 49:1166-1168 (1994) describes the use of nebulized lignocaine alone or in combination with adrenaline for suppression of capsaicin-induced cough. Lignocaine (20 mg) or a mixture of lignocaine with adrenaline (20 mg and 400 μm) significantly reduced coughing.

*Br. J. Dis. Chest*, 71:19-24 (1977) describes the use of lignocaine aerosol for treatment of intractable cough. Lignocaine (4 ml of 10%, i.e. 400 mg) was administered using a Monaghan nebulizer delivering particles between 5 and 20 μm. Inhalation took 15-20 minutes. Inhalation was repeated in intervals dictated by patient's response, in some patients every 6 weeks in others every four weeks or three weeks. Repeated inhalation was continued for half a year. The reference discloses that when nebulized lignocaine is used as an antitussive before fiberoptic bronchoscopy it suppresses cough within 10-15 minutes. However, the used nebulizer generates very large particle sizes requiring the ten times higher dose of the drug.

*Europ. J. Anaest.*, 14:616-622 (1997) describes the advantages of alkalinized lignocaine for determination of tolerance of intratracheal tube and suppression of coughing during emergence from anesthesia. Lignocaine (3 ml 4%) or alkalinized lignocaine (3 ml 4%) are administered into the trachea.

All publications described above have certain shortcomings in terms of safety, time constrains, amount of lidocaine and tolerability for inhaled lidocaine or another anesthetic. Undesirable secondary symptoms associated with the administration of lidocaine are oropharyngeal numbing with loss of gag reflex, risk of aspiration of fluids and food, moderate to severe bronchospasm, and taste problems. In addition, none of the previous treatments are short in time and efficient enough to provide rapid administration and relief from cough.

From the brief description above, it is clear that there is a continuous need for an effective and improved therapy for treatment of acute and chronic cough or tussive attacks and episodes with novel compositions and devices. Such therapy would preferably comprise an inhalation of the aerosolized anesthetic formulation delivering a therapeutically effective amount of the drug directly to the endobronchial space of airways in a shortest possible time.

It is, therefore, a primary object of this invention to provide a method for treatment of cough and/or tussive attacks and episodes by providing a safe, physiologically acceptable and efficacious formulation for inhalation using a pure, preservative free solution or dry powder comprising lidocaine or another anesthetic compound, which formulation contains a sufficient but not excessive concentration of the active drug, which solution can be efficiently aerosolized by nebulization using an electronic nebulizer into an aerosol having a MMAD substantially within a range from 3 μm to 10 μm and a substantially monodisperse particle size spectrum, or a dry powder formulation having similar aerosol properties administered by a dry powder or metered dose inhaler. Both the nebulized solution and the dry powder are well tolerated by patients.

All patents, patent applications and publications cited herein are hereby incorporated by reference.

SUMMARY

One aspect of the current invention is a solution for inhalation comprising lidocaine or another anesthetic for targeted delivery of lidocaine into conducting and central airways of the lungs for treatment of cough or tussive attacks or episodes or for improvement of tolerance for smoke, smog, dust or air pollution.

Another aspect of the current invention is a solution for inhalation for delivery of lidocaine or another anesthetic compound into conducting and central airways of the lungs, said solution nebulized into an aerosol with a MMAD substantially in the range of about 3 μm to about 10 μm and a substantially monodisperse particle spectrum with a geometric standard deviation (GDS) smaller than 1.7, wherein said solution is nebulized using an electronic nebulizer and delivering said nebulized solution by inhalation into the conducting and central airways of a subject suffering from cough or tussive attacks or episodes.

Yet another aspect of the current invention is a method for treatment of cough or tussive attacks and episodes by inhalation of lidocaine, said method comprising administration of a nebulized lidocaine solution in a dosage from about 10 mg to about 40 mg/per one dose into conducting and central airways, said solution nebulized into an aerosol with a MMAD in the range from about 3 μm to about 10 μm.

Yet another aspect of the current invention is a nebulized lidocaine solution comprising from about 10 mg to about 40 mg/per one dose of lidocaine, said aerosol having a MMAD in the range of about 3 μm to about 10 μm wherein said nebulized solution has a significantly improved lidocaine delivery to the targeted airways compared to other previously known and used lidocaine solutions.

Still another aspect of the current invention is a formulation comprising from about 10 to about 80 mg, preferably about 40 mg/per one dose, of lidocaine dissolved in a normal or diluted saline solution of from one tenth to a normal strength or in another aqueous solvent containing chloride, wherein said formulation has a pH between 5.5 and 7.0, unbuffered, osmolality between 150 and 550 mOsm/kg, ion concentration between 31 and 300 mM of chloride as a permeant anion and viscosity smaller than 1.5 cp, wherein said formulation is delivered by nebulization in about 1-5 ml of solution, wherein the resulting aerosol has a MMAD between 3 µm and 10 µm and a substantially monodisperse particle spectrum and wherein said formulation is nebulized using an electronic nebulizer.

Still yet another aspect of the current invention is a formulation of lidocaine dry powder whose particle size distribution has a MMAD between about 3.5 lam to about 10 µm with a substantially monodisperse particle spectrum for efficient deposition of lidocaine dry powder into conducting and central airways.

Still yet another aspect of the current invention is a dry powder formulation comprising from about 10 to 40 mg of lidocaine, wherein said formulation is milled, spray dried or precipitated into a fine powder with a MMAD between about 3.5 µm and 10 µm and a substantially monodisperse particle spectrum distribution wherein said dry powder formulation is used for inhalation administered from one to four times per day with a daily dose not exceeding 150 mg per day.

Another aspect of the current invention is a two-part reconstitution system comprising lidocaine in a dry or lyophilized powder form and a diluent stored separately until use.

Another aspect of the current invention is the lidocaine solution or lidocaine dry powder conveniently provided in plastic vials for storage at room temperature and easy use.

Another aspect of the current invention is a treatment of cough or tussive attacks or episodes by administering nasally, orally or intravenously an appropriately formulated lidocaine or another anesthetic wherein for nasal administration, lidocaine or the local anesthetic is formulated as drops comprising about 2.5 mg of the drug in 0.3 ml of solvent, for oral administration, 50-100 mg of the drug is administered orally once or twice daily and for intravenous administration, the daily dose is up to 2000 mg administered once or several times a day.

DEFINITIONS

Figure 1:
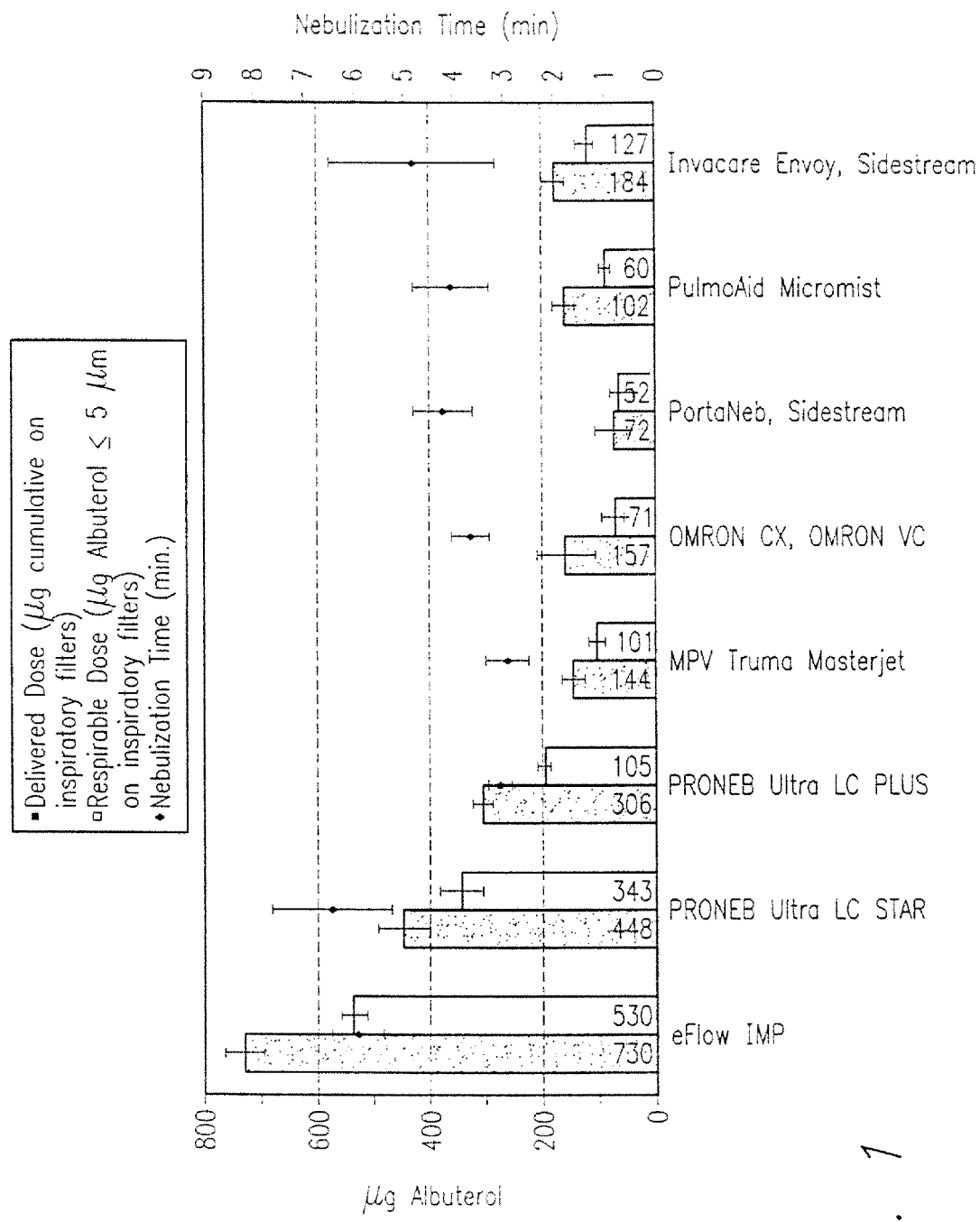
FIG. 1 shows results of comparative studies of eight different nebulizers determining a total delivered dose of the drug and respirable dose of albuterol in time.

As used herein:
"MMAD" means mass median aerodynamic diameter.
"Normal saline" or "NS" means water solution containing 0.9% (w/v) NaCl.
"Diluted saline" means normal saline containing 0.9% (w/v) NaCl diluted into its lesser strength from about 0.04% to about 0.8%.
"Half normal saline" or "½ NS" means normal saline diluted to its half strength containing 0.45% (w/v) NaCl.
"Quarter normal saline" or "¼ NS" means normal saline diluted to its quarter strength containing 0.225% (w/v) NaCl.
"One tenth normal saline" or "1/10 NS" means normal saline diluted to its one tenth strength containing 0.09% (w/v) NaCl.
"One twentieth normal saline" or "1/20 NS" means normal saline diluted to its one tenth strength containing 0.045% (w/v) NaCl.
"Physiologically acceptable solution" means a saline diluted to between 1/10 NS and 1 NS or another aqueous solution comprising from about 31 to about 154 mM of chloride.
"Composition" means a lidocaine containing formulation additionally containing other components, such as excipients, diluents, isotonic solutions, buffers, etc.
"Formulation" means a specific composition formulated for specific use, such as for nebulization of lidocaine containing solution or nebulization of lidocaine dry powder.
"Lidocaine composition" or "lidocaine formulation" means a composition or formulation comprising an indicated amount of lidocaine.
"Central airways" means a section in respiratory tract defined by trachea, carina and bronchi.
"Carina" or "carina tracheae" means the ridge separating the opening the right and left main bronchi at their junction with the trachea.
"LSI" means lidocaine solution for inhalation.
"Local anesthetic" means proparacaine, cocaine, procaine, vadocaine, tetracaine, hexylcaine, bupivacaine, lidocaine, benoxinate, mepivacaine, prilocaine, mexiletene and etidocaine.
"Predominantly" means at least 70%, but typically means 90% or more.
"Substantially" means at least 80%.
"TOR" means total output rate.
"GSD" means geometric standard deviation.

DETAILED DESCRIPTION OF THE INVENTION

The current invention concerns a discovery that a local anesthetic, and particularly lidocaine, specifically formulated and delivered as an inhalable formulation nebulized into particle sizes between about 3 µm and about 10 µm using an electronic nebulizer, is safe and efficacious for treatment of cough of any origin and particularly for treatment of tussive attacks or episodes.

Consequently, the invention concerns an inhalable composition comprising lidocaine or another local anesthetic and a method for treatment of cough, tussive attacks or tussive episodes. The inhalable composition is formulated as a dry powder or as a solution for inhalation and delivered to a patient's conducting and central airways by inhalation of a dry powder or inhalable solution nebulized into an aerosol having a MMAD from about 3 µm to about 10 µm, preferably from about 4 µm to about 5 µm, with geometric standard deviation smaller than 1.7. The inhalable composition preferably comprises lidocaine solution or lidocaine dry powder for inhalation.

The current invention thus concerns an efficacious, safe, nonirritating and physiologically acceptable and compatible inhalable anti-tussive composition suitable for treatment of cough or tussive attacks or episodes, said composition preferably comprising lidocaine as an active ingredient. The inhalable lidocaine composition is formulated for delivery as an inhalable aerosol or as an inhalable dry powder. For aerosolization, lidocaine is dissolved in a minimal volume of about 1 to about 5 ml of saline, preferably 1-2 ml of normal or diluted saline, having a pH between 5.0 and 7.5, preferably between 5.5 and 6.5, osmolality between 200 and 400 mOsm/kg, preferably between about 250 to about 300, and is nebulized into an aerosol having a mass median aerodynamic diameter (MMAD) between 3 μm to 10 μm, preferably between about 4 μm to about 5 μm, using an electronic nebulizer able to aerosolize the lidocaine solution into particles of required sizes in a time from about 1 to about 3 minutes.

I. Local Anesthetics

Local anesthetics are drugs used for the interruption of nerve transmission of pain sensations. These drugs prevent perception of pain at a site of administration. Examples of local anesthetics are proparacaine, cocaine, procaine, tetracaine, hexylcaine, bupivacaine, lidocaine, benoxinate, mepivacaine, prilocaine, mexiletene, vadocaine and etidocaine. A representative and preferred local anesthetic is lidocaine.

A. Lidocaine

Lidocaine is a local anesthetic known under the chemical name acetamide 2-(diethylamino)-N-(2,6-dimethylphenyl).

Lidocaine suitable for use in this invention is commercially available, for example from DSM Wyckoff, South Haven, Mich., and packaged by Cardinal Health Technologies-STW, Woodstock, Ill., as 1% or 4% lidocaine solution for intravenous use modified as follows.

1. Lidocaine Solution for Inhalation

In this invention, lidocaine solution for inhalation (LSI) is intended to be used in combination with a specifically modified electronic nebulizer, preferably equipped with a vibrating perforated membrane, such as and preferably the PARI eFlow® electronic nebulizer. Only in combination between LSI and an appropriate electronic nebulizer will the advantages of this invention be valid and apparent. LSI is specifically formulated for inhalation, is preservative free and optimized regarding osmolality, pH, and viscosity, to be adequate for nebulization via the electronic nebulizer.

Lidocaine solution for inhalation (LSI) is provided as a 1.0 mL sterile, preservative free, nonpyrogenic single dose. The solution contains either 10 mg (1%) or 40 (4%) of lidocaine hydrochloride, per 1 mL of a normal or diluted saline solution, having a pH adjusted to a range between pH 5.0 to 7.5. The osmolality of the solutions is preferably adjusted to between 275-300 mOsm/kg.

Lidocaine for inhalation (1% or 4%) may be delivered with or without pre-treating the patients with an inhaled beta-agonist, such as for example albuterol, further protecting the lungs from bronchospasm.

2. Lidocaine Dry Powder for Inhalation

Lidocaine for inhalation may be also formulated as a dry powder and delivered using dry powder inhalers or metered dose inhalers.

The lidocaine dry powder is prepared as a powder having a particle sizes predominantly in a range from about 3.5 to about 10 μm.

3. Lidocaine for Nasal, Oral or Intravenous Use

Properly formulated lidocaine for nasal, oral or intravenous delivery may also be advantageously used for treatment of cough or tussive attacks or episodes.

For nasal administration, lidocaine is formulated as a spray or nasal dropper. The smallest dose of lidocaine for treatment of cough nasally is 0.25%/0.3 ml once a day, administered by nasal drops or spray. The highest dose used for nasal administration is approximately 1% LSI/0.5 ml, administered 3 times daily with 10-15 mg daily dose. Preferred dose of lidocaine administered nasally is 0.5%/0.3 ml administered twice a day in 3 mg total daily dose.

For oral administration, lidocaine is formulated as a liquid or capsule with a smallest dose of lidocaine of 50 mg once a day using the commercially available oral form. The highest dose of orally administered dose is 300 mg 3 times daily up to 900 mg daily dose. Preferred dose is 100 mg twice a day with 200 mg daily dose.

Intravenous administration of lidocaine comprises the smallest dose of 0.5%/10 ml once a day and the highest dose of 2%/50 ml administered twice daily. Preferred dose for intravenous administration is 1%/20 ml once a day, that is 200 mg daily dose.

B. Other local Anesthetics

Other local anesthetics for inhalation, nasal, oral or intravenous treatments of cough are formulated similarly to the lidocaine as described above.

Lidocaine is utilized as a representative of the local anesthetics. However, all statements and description related to lidocaine are equally applicable to the other anesthetics, listed and described herein.

II. Conducting and Central Airways and Couch

The inhalation therapy of cough or tussive attacks or episodes targets areas where the cough receptors reside, namely the conducting and central airways. Conducting and central airways are comprised of trachea, carina and bronchi. The lidocaine or other local anesthetic formulation is therefore formulated in such a way as to be predominantly and preferentially deposited in these three areas.

III. Inhalable Compositions for Treatment of Cough

The current invention primarily concerns a concentrated inhalable lidocaine composition for treatment of cough or tussive attacks or episodes. Lidocaine is formulated for efficacious delivery into the connecting and central airways of the lungs by aerosolization of the lidocaine solution for inhalation or by nebulization of a lidocaine dry powder.

Lidocaine solution for inhalation is delivered by aerosolization using exclusively electronic nebulizers or dry powder inhalers that produce aerosols with a MMAD between about 3 μm and 10 μm, preferably between 4 and 5 μm, with a substantially monodisperse particle spectrum. The above indicated particle sizes are necessary for efficacious delivery of lidocaine into the central airways while a deposition and anesthetic effect of lidocaine in oral and pharyngeal area is minimized. In this regard the choice of the electronic nebulizer is critical for practicing the current invention.

Most currently available nebulizers are polydisperse and therefore produce aerosol having polydisperse particle sizes spectrum. These nebulizers are primarily designed and used for delivery of pharmaceutical drugs which need to be deposited in the peripheral airways (lower lungs) for treatment of lung diseases. To achieve such treatment, most polydisperse nebulizers produce aerosols with MMAD in the range of 1 μm to 100 μm. Some more recently developed nebulizers were shown to be able to produce particle sizes predominantly in 1 to 5 μm region. Neither the polydisperse nebulizers producing MMAD particles of unrestricted size or the nebulizers producing MMAD particle sizes from 1 to 5 μm are suitable for the method of this invention which requires maximizing aerosol deposition in the conducting and central airways and minimizing such deposition in oral or pharyngeal region or in peripheral areas of the lower lungs.

The invention is designed and developed to be used exclusively for inhalation of the solution comprising lidocaine or another local anesthetic in conjunction with an electronic nebulizer, particularly with a specifically modified electronic nebulizer PARI eFlow™. The PARI eFlow nebulizer is monodisperse and is thus able to produce predominantly monodisperse particles substantially in a range from about 3 to about 10 μm, preferably between 4 and 5 μm. A dry powder or metered dose inhalers that produce aerosols with a MMAD between about 3.5 μm and 10 μm with a preferred MMAD being between 4 μm and 5 μm are used for nebulization of the lidocaine dry powder. Such particle sizes are necessary for efficacious delivery of lidocaine into the conducting and central airways while minimizing the deposition of lidocaine anesthetic oropharyngeally and in the lower lungs.

A. Properties of Lidocaine Solution for Inhalation

Lidocaine composition for nebulization is formulated for most efficacious but safe delivery of aerosolized lidocaine to the lung conducting and central airways. In order for the lidocaine solution for inhalation to be effective for treatment or abatement of cough or tussive attacks or episodes, the solution must have certain predetermined properties, such as a certain range of pH, osmolality, viscosity, volume and concentration of the active drug. Additionally, the solution must be safe and well tolerated by patients and its delivery must be reasonably fast and efficacious.

The lidocaine composition contains 10 mg, 40 mg or, rarely and only in some instances, it may contain 80 mg, of the drug per 1-5 ml, preferably 1 ml, of saline or another solvent for one inhalation dose. When formulated and delivered according to the method of the invention, it delivers a therapeutically efficacious dose of lidocaine to a target site of cough in an amount of lidocaine sufficient to treat the cough or tussive attacks or episodes.

A combination of lidocaine composition with an electronic nebulizer that produces an aerosol with a substantially monodisperse particle spectrum, particularly the PARI eFlow nebulizer equipped with a vibrating perforated membrane (PARI GmbH, Munich, Germany), permits a delivery of a substantially whole dose of lidocaine into conducting and central airways without any substantial deposition of lidocaine into oropharyngeal space, where it is known to cause local numbing and loss of gag reflex, or into the lower lungs where it could cause undesirable side effects and easily enter the systemic circulation.

Each dose of lidocaine solution contains a minimal yet efficacious amount of either 10 or 40 mg of lidocaine, per one ml dose, formulated in the smallest possible volume (1 ml) of saline, said solution having osmolality between 275 and 300 mOsm/Kg, viscosity about 1.5 cp and pH between 5.0 and 7.5, preferably the pH of about 5.5-6. Thus formulated lidocaine solution for inhalation generates a lidocaine aerosol that is safe and well tolerated by patients and minimizes the development of secondary undesirable side effects such as bronchospasm, loss of gag reflex or numbing and has a minimal oropharyngeal deposition.

1. Safety

Primary requirement for the aerosolized local anesthetic formulation is its safety. Safety is measured by the anesthetic effect of the local anesthetic asserted on the other areas of the respiratory tract and by its deposition in the other areas of the respiratory tract than those where cough occurs and by its numbing effect. Bronchospasm of the lung in cough is a one of the most observable symptoms, as described amply in the literature, and it is therefore important that the administration of lidocaine to the upper lungs does not result in or further aggravate bronchospasm due and related to any preservative contained in the inhalable lidocaine solution, or is not related to or caused by the particle sizes of the lidocaine aerosols. With a non-targeted delivery of lidocaine into the lungs, side effects such as systemic effects on the central nervous system, headache, tremor and dizziness are known to occur and are a measure of safety.

Since the lidocaine for inhalation is formulated to contain only a nominal amount of lidocaine and since it is delivered in particle sizes predominately deposited in targeted lung areas, the method for treatment of cough or tussive attacks or episodes is both safe and efficacious.

2. Efficacy

Efficacy is measured by the amount of the drug needed for cough abatement, by the frequency of administration needed to suppress tussive attacks or episodes, by the time necessary for delivery of the drug amount and by the percentage of the drug deposited in the specific target areas, namely in trachea, carina and bronchi as well as a lack of deposition in the other areas, namely in the upper airways, such as mouth, nose, larynx and pharynx and in the lower lungs, such as bronchiole and alveoli. Very importantly, efficacy is measured by the patients' tolerance to environmental challenges to the airways, and his/her tolerance to smoke, smog, dust, allergens and air pollution.

Main advantages of the current lidocaine formulation are its safety, its efficacy in cough abatement, its lesser anesthetic effect, its lesser oropharyngeal deposition, its lack of bronchospasm, its faster delivery and its targeted dosing, practicality and convenience of use as well as its long shelf-life, storage and ease of administration and manipulation of the nebulization device. Because of convenience, safety and practicality of the formulation and the nebulizer, the treatment may be provided in hospital setting, in the doctors office or at home.

Both the safety and efficacy requirements for aerosolized lidocaine have now been found to be met by the lidocaine formulation described herein.

3. Tolerability

The key parameters for airway tolerability of the lidocaine formulation for inhalation during aerosolization exposure which needs to be met are osmolality, pH, lidocaine concentration, ion concentration, viscosity and the absence of preservatives. These parameters are listed in Table 1, below.

TABLE 1

| Tolerability Parameters of Inhalable Lidocaine | |
| --- | --- |
| Osmolality | >150-<550 mOsm/kg |
| Ion Concentration | >31-<300 mM permeant anion |
| pH | 5.5 to 7.0, unbuffered |
| Viscosity | <1.5 cp |
| Drug Concentrations | 1-4% lidocaine HCl |
| Surfactant | None |
| Preservatives | None |
| Nebulization Time | <1-2.5 minutes |

As seen in Table 1, the lidocaine solution of the invention has osmolality between 150 and 550 mOsm/kg, ion concentration between 31 and 300 mM of the permeant anion, pH between 5.5 and 7.0 and viscosity lower than 1.5 centipoise. The lidocaine concentration is either 10 or 40, rarely 80, mg per ml of saline. Other than saline, there are no other preservatives which could cause secondary side effects. Nebulization time for administration of one ml of the lidocaine solution is about 1-2.5 minutes when delivered with an electronic nebulizer on the output rate of the PARI eFlow electronic nebulizer which has total output rate (TOR) higher or equal to 0.4 g/minute. When the output rate is about 0.5 g/minute, the delivery of 1 ml of the lidocaine formulation is shortened to less than 2 minutes.

From the above description is it clear that the lidocaine formulation for inhalation, as described herein, combined with the electronic nebulizer having the above described characteristics, delivers the efficacious amount of lidocaine into lungs of the patient within one to two minutes and at most at 2.5-3 minutes. The exposure of the patient to lidocaine is thus substantially shortened compared to all prior inhalation attempts with lidocaine and such treatment is, therefore, better tolerated.

4. Dosage of Lidocaine

The effective treatment of cough or tussive attacks or episodes requires a treatment regimen which provides sufficient amount of drug to suppress the coughing. Such regimen requires administration of an inhalable lidocaine one to up to four times a day. Most preferred dosing regimen for patient convenience is once or twice a day, however, because of a specific anesthetic effect of lidocaine asserts on the lungs and because of its relatively short life-time of about 2.5 hours, sometimes more than twice a day dosing is required for complete management of cough or tussive attacks or episodes. While typically, for the treatment of cough according to the invention a twice-a day regimen is sufficient, the lidocaine formulation may be safely administered for and up to ten times-a day either in 10 or 40 mg dose.

A total daily dose of lidocaine is therefore set to be between either about 10 or about 160 mg per day administered in one or more doses of 10 or 40 mg per one dose. The total maximum recommended daily amount should typically not exceed about 200 mg.

Typically, the formulation and the electronic nebulizer are selected to provide at least about 25-40%, preferably higher than 50% efficacy of lidocaine delivery to the conducting and central airways. Thus, with 10 or 40 mg dose, between 2.5 to 4 mg is delivered if the dose is 10 mg/ml. When the dose is 40 mg, the delivered amount of lidocaine into lungs is between 10 and 16 mg of during each administration. Three mg of lidocaine delivered to the lung has been found to be efficacious in patients suffering from seasonal non-severe cough. For suppression of severe chronic cough, the 16 mg dose delivered as a 40 mg dose/1 ml of saline according to the invention, is very efficacious, and since it can be delivered in a very short period of time of less then 2 minutes, it was found to be void of any severe undesirable effects, such as numbing of the oropharyngeal area, loss of gag reflex or increased systemic plasma levels. In no instance should one dose exceed 80 mg lung dose.

Determination of the effective dosage of administered lidocaine and the regimen used for treatment of each patient depends on the responsiveness of the individual patient to the treatment. The ultimate decisive factor is the expected level of lidocaine in the area where cough receptors are located after aerosolization. In addition, the lung dose is also correlated with lidocaine plasma levels. The optimal range of lidocaine in 1 ml of plasma immediately after nebulization should be in the 20-500 ng/mL range. Thus, the frequency of the administration is correlated with the effectiveness of administered lidocaine.

The new mode of administration permitting a noninvasive administration of small yet effective amounts of lidocaine directly into conducting and central airways provides substantial improvement compared to all previously known method used for delivery of nebulized lidocaine.

5. Effect of pH on Lidocaine Aerosol Formulation

The pH of the nebulized formulation containing lidocaine is an important feature for treatment of cough. Consequently, the saline solution used for preparation of lidocaine aerosol has certain requirements. Such aerosol has to provide osmolality between 275 and 300 mOsm/kg and not to affect the pH range, which is from 5.5 to 7.0, preferably between pH 5.5 and 6.5.

The control of pH of the LSI formulation is necessary for efficacious delivery of the nebulized lidocaine. When the lidocaine aerosol is either more acidic or basic, that is outside of the range of pH given above, it can cause bronchospasm in central airways and exacerbate the cough. Although the safe range of pH is relative and some patients may tolerate a mildly more acidic aerosol, others will experience bronchospasm. Any aerosol with a pH of less than 4.5 typically induces bronchospasm. Aerosols with a pH between 4.5 and 5.5 will cause bronchospasm occasionally. Testing of lidocaine aerosol discovered that an aerosolizable lidocaine formulation having a pH between 5.5 and 7.0 is well tolerated and safe. Any aerosol having pH greater than 8.5 is to be avoided as the lung epithelium is unable to buffer larger amounts of alkaline aerosols. Aerosol with pH below 4.5 and over 8.5 result in lung irritation accompanied by severe bronchospasm, exacerbated cough, and inflammatory reactions.

For these reasons as well as for the avoidance of bronchospasm, cough or inflammation in patients, the optimum pH for the lidocaine aerosol formulation was determined to be between pH 5.5 to pH 7.0 with tolerable pH between pH 5.0 and 7.5. Consequently the lidocaine aerosol formulation is adjusted to pH between 5.5 and 7.0 with preferred pH range from about 5.5 to 6.5. Most preferred pH range is from 5.5 to 6.

6. Effect of Salinity on the Lidocaine Formulation

Patients suffering from acute or chronic cough, particularly those with chronic cough and recurring tussive attacks or episodes, have increased sensitivity to various chemical agents and high incidence of bronchospasm. Since this method is designed for treatment of cough, the salinity of the local anesthetic solutions is very important.

The airways of the patient suffering from cough are particularly sensitive to hypotonic or hypertonic and acidic or alkaline conditions and to the excess but also the absence of a permanent ion chloride. Any imbalance in these conditions or a presence of chloride above certain values leads to bronchospasm or inflammatory events and/or exacerbated cough which greatly impair treatment with inhalable formulations. All these conditions prevent efficient delivery of aerosolized lidocaine into the central airways. The bronchospasm and inflammatory clinical manifestations of the irritated airways are extremely undesirable for a method of treatment of cough or tussive attacks or episodes according to this invention.

The use of aqueous solvents for lidocaine formulation without providing certain degree of osmolality to emulate physiological conditions found in healthy lungs is undesirable.

Consequently, a certain amount of the chloride anion is needed for successful and efficacious delivery of aerosolized lidocaine and such amount is much more specific than amounts provided and typically used for aerosols of other compounds. Persistent or severe cough is often accompanied by bronchospasm that does not readily respond to the same osmolality of the diluent used for aerosolization. However, it has been now found that such bronchospasm can be sufficiently controlled and/or suppressed when the osmolality of the diluent is in a certain limited range. Consequently, the preferred solution for nebulization of lidocaine suitable for treatment of persistent and severe cough that is safe and tolerated has a osmolality limited to between 275 and 300 mOsm/kg with a range of chloride concentration of between 31 mM and 300 mM. The given osmolality controls bronchospasm and the chloride concentration, as a permeant anion, contributes to the control of cough or tussive attacks or episodes.

Normal saline (NS, 0.9%) contains 154 mM of chloride whereas 31 mM of chloride corresponds to about 0.2% normal saline. Lidocaine salt is manufactured as lidocaine HCl.

Higher concentrations of lidocaine solution for inhalation therefore needs lesser addition of NaCl, in order to reach the 150 mM chloride content.

It has now been discovered that lidocaine may be efficaciously delivered into the central airways when dissolved in lesser than normal saline, that is saline containing 0.9% of sodium chloride. The ½₀ N saline permits and assures a delivery of lidocaine into central airways and in some cases permits better particles deposition and treatment of cough.

Consequently, the formulation for lidocaine aerosol of the invention comprises either about 10 or about 40 mg, preferably about 40 mg, of lidocaine dissolved in 1 ml of a normal or a diluted saline to from about ½₀ normal saline (NS) to about and at most to 1 normal saline solution.

The lidocaine formulation containing about 10 mg of lidocaine per 1 ml of 0.2 NS has an osmolality of about 290 mOsm/l. Such osmolality is within a safe range of aerosols suitable for administration to patients suffering from cough and also those patients with chronic cough.

Since the delivery of lidocaine formulated as described herein is much more efficacious, much lower total dose of lidocaine is needed to achieve complete and fast suppression of cough. Typically, about 40 mg total dose of lidocaine dissolved in 1 ml of solution is sufficient in suppressing the severe and persistent cough when delivered with an electronic nebulizer as described above.

7. Osmolality

The osmolality of an aerosolized solution is directly related to the initiation of bronchoconstriction during inhalation. Cough is regularly induced by inhalation of solutions with osmolality <100 or >1100 mOsm/kg.

A study of 9 patients with mild asthma accompanied by cough has shown that hyperosmolar solutions, such as 4% sodium chloride (1232 mOsm) or hyperosmolar solutions, for example distilled water, (zero mOsm) induced bronchoconstriction when nebulized aerosol was inhaled. Conversely, isoosmolar solutions (308 mOsm) did not induce bronchoconstriction. Therefore, an isotonic solution, such as 0.9% sodium chloride or lesser percentage of, to compensate for hydrochloride salt would be least likely to cause bronchoconstriction.

Another point of consideration is the effect of nebulization on the osmolality of the solution. During nebulization, osmolality can increase 11% to 62%, as compared with the pre-nebulization value. The peak increase in osmolality is typically observed between 10 and 15 minutes of nebulization. This rise in osmolality may be explained by the mechanisms of nebulization. In a jet nebulizer, the aerosol is produced by the fluid shearing in a high velocity stream of dry gas. After generation of primary droplets, water evaporates from the surface of the aerosol droplets to humidify the air thereby increasing the osmolality in the droplets. Approximately 99% of the droplets then return to the reservoir causing a continuous increase in the concentration of the solute in the liquid remaining in the nebulizer and a continuous increase in the osmolality of the aerosol droplets.

Because of this observable increase in osmolality, the nebulization time was aimed to be restricted to no more than 10 minutes. Of course, when the nebulization is performed in the shorter time, as in the current invention, where the time for nebulization is typically between 1 and 2 minutes and is limited to at most to 3 minutes, none or only a small increase in osmolality occurs.

Selection and exclusive use of the electronic nebulizer, such as for example, PARI e-Flow or one of the other similarly equipped electronic nebulizers, results in shortening of the time for nebulization to 1-2 minutes, thereby eliminating or negating the concentration effect observed with other types of nebulizers and no drug concentration occurs during nebulization.

8. Ion Concentration and Permeability

The absence of permeant anion in ultrasonically nebulized solutions is a stimulus for cough even under isoosmolar conditions, and the amount of cough is directly proportional to the concentration of permeant anion. Therefore, not only is the ion concentration important for airway tolerability, but the type of the ion present must also be considered. Inhalation of a solution with osmolality between 225 and 616 mOsm/kg induces cough when the chloride concentration is less than 31 mM. Chloride was found to be an ideal permeant ion, with its presence mitigating some of the adverse effects caused by the hypertonicity of nebulized solutions. A chloride concentration between 31-300 mM was found to be optimal. If the ion used is not chloride, the selected alternative anion should freely permeate the respiratory mucosa.

Examples of salts that produce suitable permeant anion and can be thus used as a substitute of the sodium chloride are calcium chloride, choline chloride, lysine monohydrochloride, potassium chloride, sodium chloride, sodium bromide and sodium iodide.

However, while it is possible to use these substitutes, for the purpose of this invention, the sodium chloride anion is most preferable.

9. Viscosity

The rate of nebulization and particle size distribution is directly proportional to the viscosity of the solution, as when the rate of nebulization and particle size decrease, the viscosity increases.

Concentrations of antibiotic solutions that produced viscosities greater than 1.5 cp were found to have a dramatic impact on the nebulization rate. Consequently, the viscosity of the lidocaine solution for inhalation was set to and should be kept near 1.5 cp.

10. Additives

As already stated above, the lidocaine solution for inhalation is preservative free and preferably no other additives are used.

Any use or intent to use additives will require careful consideration concerning its effects on the airway tolerability and toxicity of the solution.

11. Preferred Aerosolizable Lidocaine Formulations

Patients suffering from cough or tussive attacks or episodes can be sensitive to pH, osmolality, and ionic content of a nebulized solution. Therefore these parameters are adjusted to be compatible with lidocaine chemistry and still tolerable to patients.

The preferred formulation of the current invention is a formulation comprising either about 10 or about 40 mg of lidocaine dissolved in from about 1 to about 5 ml of saline, having pH adjusted to between 5.5 and 7.0, delivered by nebulization in an aerosol having a mass median aerodynamic diameter (MMAD) between 3.0 μm and 10 μm, wherein said formulation is nebulized using an electronic nebulizer preferably equipped with a vibrating perforated membrane.

The most preferred formulation of the current invention comprises about 10 or 40 mg dose of lidocaine dissolved in about 1 ml of saline, having pH adjusted to between pH 5.5 and 5.5, delivered by nebulization in aerosol particles having the mass median aerodynamic diameter (MMAD) predominantly between 3 and 10 μm, preferably 4 μm and 5 μm, wherein said formulation is nebulized using a PARI eFlow electronic nebulizer, particularly the one equipped with a vibrating perforated membrane.

Table 2 shows these and other preferred parameters for two specific lidocaine formulations.

TABLE 2

Parameters 1% and 4% Lidocaine Solution For Inhalation

|  | 1% Lidocaine HCl | 4% Lidocaine HCl |
|---|---|---|
| [Cl−] mM | 153 | 153 |
| Osmolality mOsm/kg | 291 | 286 |
| pH | 6.4 | 6.2 |
| ppm (Na+) |  | 160 |
| surface tension dynes/cm = mN/m |  | 58.32 |
| viscosity cps | 1.39 | 1.33 |
| Density | 1.00315 | 1.00239 |
| % label claim | 99 | 100 |

All formulations are designed to be well tolerated and able to be reliably and completely nebulized to aerosol particles within the respirable size range of 3 μm to 10 μm, preferably within 4 μm and 5 μm, deposited rapidly within 1-2 minutes and predominantly into the conducting and central airways.

The doses are designed to contain as much as, but not more than, the necessary amount of a most active form of lidocaine to prevent and treat severe cough and tussive attacks and episodes.

The formulation of the invention is nebulized into an aerosol with characteristics optimizing a delivery of the drug into the central airways where cough receptors are located and cough originates.

For efficacious delivery of lidocaine to the lung central airways in the aerosol, the formation of an aerosol having a mass median aerodynamic diameter (MMAD) between 3.5 μm to 10 μm, preferably between about 4 μm and about 5 μm, is necessary. The formulated and delivered amount of lidocaine for treatment of cough must effectively target the lung conducting and central airways. The formulation must have a smallest possible aerosolizable volume able to deliver an effective dose of lidocaine in the shortest possible time. The formulation must additionally provide conditions which would not adversely affect the functionality of the central airways. Consequently, the formulation must contain enough of the drug formulated under the conditions which allow its efficacious delivery while avoiding numbing of upper respiratory tract and deposition in lower areas of lung not affected by cough. The new formulation according to the invention meets all these requirements.

B. Lidocaine Dry Powder Composition

An alternative way to deliver inhalable lidocaine for treatment of cough or tussive attacks or episodes is by way of dry inhalable powder administered to the connecting and central airways dry powder or metered dose inhalers.

A dry powder formulation comprises from about 10 to 80 mg, preferably 40 mg of lidocaine, and has potency, on a mass basis, allowing delivery of a sufficient amount of lidocaine dry powder using dry powder inhaler or metered dose inhaler into a lung target area. For delivery of the dry inhalable powder, lidocaine is milled, precipitated, spray dried or otherwise processed to particles that when emitted from the dry powder inhaler form an aerosol with a mass median aerodynamic diameter between about 3.5 μm and 10 μm, preferably from about 4 μm to about 5 μm. Examples of powder processing technologies include, but are not limited to media milling, jet milling, spray drying or particle precipitation techniques.

In this aspect, the dry powder inhaler or metered dose inhaler is practical and convenient as a means of lidocaine dry powder delivery means because it does not require any further handling such as diluting the dry powder or filling a nebulizer. Furthermore, the dry powder or meter dose inhalers are small and fully portable units.

The dry powder formulation is thus practical and convenient and particularly suitable for ambulatory use because it does not require dilution or other handling, it has an extended shelf-life and storage stability and the dry powder inhalation delivery devices are portable and do not require large attachments needed by aerosol nebulizers.

All techniques suitable for preparation of dry inhalable powders and any and all improvements thereof as well as any dry powder inhaler or any other inhaler suitable for delivery of the dry powder are intended to be within the scope of the invention.

C. Shelf-Life and Storage

Stability of the formulation is another very important issue for efficacious formulation. If the drug is degraded before nebulization, a smaller amount of the drug is delivered to the lungs thus impairing the treatment efficacy. Moreover, degradation of stored lidocaine may generate materials that are poorly tolerated by patients.

The dry form, that is lyophilized lidocaine for preparation of a lidocaine solution for inhalation or a lidocaine dry powder, has at least 2 years long shelf life. According to the invention, lidocaine for aerosolization is preferably formulated in a predetermined lyophilized dosage form of 10 or 40 mg intended for reconstitution before inhalation therapy. The formulation of lidocaine can thus be aseptically prepared as a lyophilized powder either for dry powder delivery or for reconstitution, as a frozen solution, a liposomal suspension or as microscopic particles. The extended shelf-life provides for easy and reliable storage of the formulation and allows easy reconstitution or use of the lidocaine in dry form suitable for aerosolization.

The lidocaine solution for inhalation suitable for aerosolization is preferably provided as two separate components, one containing a dry lidocaine lyophilizate or powder, or a salt thereof, and a second containing an appropriate diluent such as from 0.1 to 0.9 N saline, as described above. The solution for inhalation is reconstituted immediately prior to aerosolization and administration to the patient. The two component packaging for storage prevents problems connected with the long-term stability of lidocaine in aqueous solvents.

The liquid form of lidocaine (1% and 4%) may also be conveniently supplied as a ready to use formulation stored and supplied in 1 ml "Blow-Fill-Seal" vial, made of plastic polyethylene material, such as low density polyethylene (LDPE) vials obtained from, for example, Huntsman Rexene 6010. Overwrap for the Blow-Fill Seal is made of Flex-icon Flexi-2114. The selected material for such ready to use formulation prevents absorption of lidocaine onto the plastic walls of the vial, which is a common occurrence with other plastic materials. The 1 ml fill volume of the vials provide an exact amount of drug, that is safe and efficacious for the patient convenience. In the above described type of vials covered with an aluminum overwrap, lidocaine solutions for inhalation (1% or 4%) are stable for at least 9 months and 12 months, respectively, at room temperature. There is no loss of strength under these conditions. At accelerated conditions where the vials are exposed to a temperature of 4000 and 75% relative humidity, both formulations were shown to retain their full activity for at least 6 months.

IV. Administration of Local Anesthetics by Inhalation

For treatment of cough or tussive attacks or episodes, local anesthetics, preferably lidocaine, formulated as described above, are administered by nebulization using the electronic nebulizer.

A. Two Modes of Inhalable Administration

Administration of inhalable lidocaine or another local anesthetic for treatment of cough or tussive attacks or episodes according to the current invention is achieved either with aerosolized lidocaine solution for inhalation or with inhalable dry lidocaine powder, as described above. The drug may be prepared and stored as a solution for inhalation, as a lyophilizate or powder and dissolved in saline just before administration, or as a powder to be used directly for administration.

B. Frequency of Dosing

The frequency of dosing is dependent on the severity or occurrence of tussive attacks or episodes of cough as well as on other conditions, such as a presence of another underlying disease, for example, asthma, chronic obstructive pulmonary disease, emphysema, lung cancer, GER, pneumonia, common cold or flu.

A treatment regimen provides for one to several, preferably four, times a day administration of the inhalable local anesthetic, such as lidocaine. Most preferred dosing regimen for patient convenience is once or twice a day, however, because of the rapid lidocaine cough suppressing effect, and because of its relatively short life-time of about 8 hours (plasma half life of lidocaine upon aerosolization is 2.5 hours), more often dosing may be required for complete suppression of cough.

In patients with severe and persistent cough, tussive attacks or tussive episodes, the frequency of dosing may be increased up to about ten-twelve times a day each time, or on an as needed basis provided that only such amount of lidocaine as necessary to suppress cough is used each time.

The lidocaine dose administered by inhalation is typically limited either to 10 or 40 mg of lidocaine per one dose. The daily dose can be as small as 10 mg with a typical upper daily limit of 160 mg with a maximum daily dose typically not exceeding 200 mg of lidocaine delivered in multiple administrations. In extreme and rare instances of very severe and persistent cough, the dose may reach up to 400 mg per day delivered in small increments in four or more successive administrations. Typical and preferred range for one aerosol dosage is between 10 and 40 mg administered twice a days or 40 mg administered three or four times per day. For a dry powder inhalation, the dose for one administration is typically between about 5 and 20 mg per one dose and at maximum can reach 200 mg per one dose. The frequency of dosing is typically three or four times a day but also includes one or two or more than four times dosing regimen as this regimen depends on the need and condition of the patient.

Patients with severe cough, asthma, bronchospasm or those patients experiencing, for example, cough after surgery, may be able to withstand only one very short inhalation at a time but such inhalation could be repeated with a smaller amount of lidocaine every two, three or four hours to obtain sufficient level of lidocaine to suppress cough without causing or worsening patient's bronchospasm or other conditions.

V. Devices for Delivery of Aerosolized Lidocaine

A primary requirement of this invention is to deliver lidocaine efficiently to the central airways in a most rapid, efficient and economic way. Drug delivery to the lungs is a function of the size distribution of the inhaled aerosol, the delivery system, and the drug content of the particles. The effects of these aspects are well documented in the literature ("The Mechanics of Inhaled Pharmaceutical Aerosols" by W. H. Finlay, Academic Press, 2001).

A. Nebulizers

The composition of the invention described above provides the local anesthetic, preferably lidocaine, formulated in a solution permitting delivery of a therapeutically efficacious amount of the drug, provided that the aerosol generated by the nebulization meets criteria required for such efficient delivery. The electronic nebulizer which aerosolizes the formulation of the local anesthetic, and particularly lidocaine, according to the invention, is an indivisible part of the invention.

There are quite a few nebulizer types currently commercially available. None of them but the electronic nebulizers are suitable for practicing this invention. "Electronic nebulizer" is defined as one of the nebulizers from the group defined and indicated as such below.

Most pharmaceutical aerosols have particle size ranges between 1 μm and 100 μm as this size range has the best balance of inhalability and ability to transport the drug. Within this range, smaller particles tend to deposit deeper in the lungs, middle size particles tend to deposit in the central lungs and larger particles tend to deposit in the mouth and throat. Since the small particles contain much less drug (mass increases as the cube of the diameter) the time to deliver an efficacious dose of drugs to the lungs is much longer with smaller particles. In such a system, a selective delivery of the drug to any one part of the respiratory system is problematic.

For deposition in the conducting and central airways, a particle size of approximately 4.5 microns is optimal. The advantage of the monodisperse electronic nebulizers, with a preferred nebulizer being the PARI eFlow nebulizer, is that the particle size distribution can be adjusted and tuned to produce particles predominantly in a range having an optimal size and deliver the drug selectively and as quickly as possible to the target area.

The most currently available pharmaceutical nebulizers produce polydisperse aerosols. Polydisperse aerosols consist of many particle sizes and consequently, the aerosols that are more polydisperse tend to deposit the particles over a wider region of the respiratory tract with a lesser dose of the drug deposited to the targeted area. The aerosol produced by the eFlow is monodisperse producing an aerosol with particle sizes having a geometric standard deviation (GSD) smaller than 1.7. Consequently, the majority of the aerosol particles are of the sizes between 3 and 10 with a large portion, typically between 70 and 90% of these particles having a MMAD between 4 and 5 μm.

The advantage of using an electronic nebulizer that produces an aerosol with the preferred characteristics is that more drug is deposited to the site of action, that is to central airways with lesser residue deposited to the mouth and throat where it would cause numbing or in the lower lungs where it could enter the systemic circulation.

Although the dry powder and metered dose inhalers are suitable and contemplated to be used for delivery of the dry powder, an electronic nebulizer is preferable over these inhalers as there is no ballistic component of the aerosol exiting the device to cause excessive deposition in the mouth and throat. It also does not require the patient to achieve the high inhalation flow rates required to efficiently use many dry powder inhalers.

The main advantage of the electronic nebulizers such as PARI eFlow over other nebulizers is the speed of delivery.

The PARI eFlow can produce aerosol much faster than other nebulizers, decreasing the treatment time substantially. Also, in comparison to other nebulizers, the eFlow has much smaller drug residue left in the device after the treatment (residual volume), increasing the efficacy of the delivery and decreasing the cost of the therapy.

By combining all these aspects, the PARI eFlow or another comparable electronic nebulizer can deliver a dose of medication to the lungs 2-5 times faster than jet nebulizers, and 2-30 times faster than regular nebulizers, while decreasing side effects due to aerosol not deposited at the other regions of the respiratory tract.

The electronic nebulizer generally and PARI eFlow nebulizer particularly is, therefore, most preferred nebulizer primarily on the basis of allowing the formation of lidocaine aerosol having a mass medium average diameter predominantly between 4 µm to 5 µm and a substantially monodisperse particle spectrum.

This aspect of the invention is of great importance because for treatment of severe and persistent cough or for treatment of tussive attacks or episodes, because the delivered amount of lidocaine must be efficacious and the delivery must be fast to avoid development of bronchospasm due to anesthetic properties of lidocaine. The selected nebulizer thus must be able to efficiently aerosolize the formulation which has salinity, viscosity, osmotic strength, and pH adjusted according to the invention as to permit generation of lidocaine aerosol that is therapeutically effective and well tolerated by patients. The electronic nebulizer must be able to handle the formulation having a smallest possible aerosolizable volume and still be able to deliver effective dose of lidocaine to the site of the action. Additionally, the aerosolized formulation must not impair the functionality of the upper airways or lower lining spots and must minimize undesirable side effects.

The inability of certain nebulizers to nebulize therapeutic quantities of drugs into uniform predetermined particle size aerosols is well known. For efficacious delivery of lidocaine a range of aerosolized particles with MMAD needed to deliver the drug to the central airways only, the site of the cough receptors, is between 3-10 µm. Many commercially available nebulizers are able to aerosolize large volumes of the solution with an aim to deliver at least 10% of the volume to the lung by producing around 90% of large aerosol particles above 10µ with a very large number of particles being in the range of 50-100 µm. These nebulizers are inefficient and not suitable for delivery of lidocaine according to this invention.

Previously, certain types of nebulizers, such as jet and ultrasonic nebulizers, have been shown to be able to produce and deliver aerosols with MMAD of between 1 µm and 5 µm. These aerosols might be optimal for treatment of pulmonary bacterial, viral or parasitic infections affecting the lower lungs, however, they are not sufficiently efficacious and selective in producing particles which are deposited predominantly in the conducting and central airways. Additionally, these nebulizers typically need larger volumes to administer sufficient amount of drug to obtain a therapeutic effect. Typically, for example, the jet nebulizers are only about 10% efficient under clinical conditions. The amount deposited and absorbed in the lungs is thus a fraction of the 10% in spite of the large amounts of the drug placed in the nebulizer.

TABLE 3

| NEBULIZER | Time/ Min. | Delivered Dose (µg) | Respirable Dose (µg) | Efficacy % |
|---|---|---|---|---|
| eFlow | 6 | 730 | 536 | 100% |
| Pro Neb Ultra LC Star | 6.5 | 445 | 343 | 61% |
| Pro Neb Ultra LC Plus | 3.5 | 306 | 195 | 42% |

TABLE 3-continued

| NEBULIZER | Time/ Min. | Delivered Dose (µg) | Respirable Dose (µg) | Efficacy % |
|---|---|---|---|---|
| MPV Truma Masterjet | 3.3 | 144 | 101 | 20% |
| OMRONCX: OMRONVC | 3.9 | 157 | 71 | 21.5% |
| Porta Neb Sidestream | 4.5 | 71 | 53 | 9.7% |
| Pulmo Aid Micromist | 4.2 | 162 | 90 | 22% |
| Invacare Envoy Side Stream | 5 | 184 | 127 | 25% |

TABLE 4

| 16 NEBULIZER | Time/ Min. | Delivered Dose | µg | Respirable Dose |
|---|---|---|---|---|
| eFlow | 6 | 730 | 100% | 536 | 100% |
| Pro Neb Ultra LC Star | 6 | 411 | 56% | 317 | 59% |
| Pro Neb Ultra LC Plus | 6 | 524 | 72% | 334 | 62% |
| MPV Truma Masterjet | 6 | 262 | 35% | 184 | 34% |
| OMRONCX: OMRONVC | 6 | 242 | 33% | 109 | 20% |
| Porta Neb Sidestream | 6 | 192 | 26% | 71 | 13% |
| Pulmo Aid Micromist | 6 | 231 | 31.5% | 128 | 24% |
| Invacare Envoy Sidestream | 6 | 220 | 30% | 152.4 | 28% |

In vivo deposition studies have demonstrated a whole lung deposition of approximately 40% of the total dose for electronic nebulizers, a marked increase in delivery efficiency compared to approximately 12% of the total dose administered with the PARI LC PLUS nebulizer.

Additionally, the oropharyngeal deposition is estimated at 5 to 10%, which is substantially lower than that of jet nebulizers (e.g., approximately 16% with the PARI LC PLUS). Further, the eFlow nebulizer's output of 8 to 10 µL/sec enables delivery of drug material 2-4 times faster than the PARI LC PLUS. The basic performance specifications for the eFlow nebulizer are presented in Table 5.

TABLE 5

Performance Specifications for PARI eFlow Nebulizer

| NEBULIZER | Value |
|---|---|
| Mass Median Diameter (MMD) | 3.3-3.8 µm |
| Geometric Standard Deviation (GSD): | approx. 1.6 µm |
| Total Output Rate (TOR) | >0.4 g/min |
| Residual Volume | negligible* |

The PARI eFlow nebulizer is designed to aerosolize the whole 1 ml of the lidocaine solution placed in the device with allowance for a maximum of 150 µl of precipitation remaining on the device walls.

The combination of these benefits results in a treatment time of one tenth to less than half of current therapies, and potentially as low as 1-1.5 minutes per nebulization of 1 mL of LSI solution.

TABLE 6

Phaser Nebulizer Performance Tests In vitro

| | Value |
|---|---|
| Phaser with 14.6% Lidocaine | |
| Lidocaine Concentration | 146.5 mg/ml |
| Actuation volume | 16 µl |

TABLE 6-continued

Phaser Nebulizer Performance Tests In vitro

| | Value |
|---|---|
| Filter deposition | 2.03 ± 0.08 |
| Mg Particles 2.1-9 μm | 89% |
| Phaser with 17.5% Lidocaine | |
| Lidocaine Concentration | 175 mg/ml |
| Actuation volume | 16 μl |
| Filter deposition | 2.46 ± 0.18 mg |
| Particles 2.1-9 μm | 72% |

In testing another nebulizers, seen in Table 6, lidocaine solution for inhalation, 14.6% and 17.5%, at 28.3 L/min, R=585 Ohm-m) were nebulized in vitro with the Battelle HH5 Phaser nebulizer. The particle sizes of the aerosol as well as deposition of the drug on a filter corresponding to inhaled dose were measured upon multiple actuations.

Results of the test with 17.5% lidocaine (175 mg/ml, 16 ul per actuation, nominal dose of 2.8 mg), show deposition of the drug on inhalation filters between 2.15 and 2.67 mg (mean 2.46±0.18 mg, RSD 7.16%) per actuation. The particle size distribution of all particles was between 2.1 and 9 μm with 72% of particle size distribution having sizes between 3.65 and 5.07 μm.

Results of the test with lidocaine 14.6% (146.5 mg/ml, 16 ul per actuation, nominal dose of 2.34 mg), show deposition of the drug on inhalation filters between 1.86 and 2.13 mg (mean 2.03±0.08 mg, RSD 3.85%) per actuation. The particle size distribution of all particles was between 2.1 and 9 μm with 89% of particles having sizes between showed 3.69 and 4.13. These studies show that the Battelle HH5 Phaser nebulizer could potentially be used for the current invention, however, there could be certain loss of the drug due to certain percentage of the particles being smaller than 3 μm.

Preferable electronic nebulizers are those electronic nebulizers that can produce aerosols with MMAD between about 4 and 5 with a relatively monodisperse particle spectrum (GSD<1.7). Examples of suitable electronic nebulizers are Aerogen Aeroneb Pro, Aerogen AeroNeb Go, Batelle White Phaser and its derivatives, Boehringer Spiromat, and preferably the PARI eFlow nebulizer. All these nebulizers can be used in practicing this invention.

The most preferred is the PARI eFlow nebulizer manufactured by PARI GmbH of Starnberg, Germany, equipped and modified with a vibrating membrane. However, it is to be understood that while preferred, the PARI eFlow is only one of the possible electronic nebulizers suitable for use in this invention.

Comparative study of the PARI eFlow electronic nebulizer delivering 1 ml, 2 ml and 3 ml doses of lidocaine or a lidocaine-like compound vis-a-vis a time of delivery, is shown in Table 7.

TABLE 7

| Drug Delivery by the Modified PARI eFlow Nebulizer | | | |
|---|---|---|---|
| | Fill Volume | | |
| | 1 mL | 2 mL | 3 mL |
| Number of PARI eFlow tested | 1 | 9 | 1 |
| Number of tests | 2 | 18 | 2 |
| Nominal Drug Dose (mg) | 92 | 184 | 276 |
| DD (mg/drug/insp. filter) ± SD | 48.9 | 98.3 ± 2.6 | 148.8 |
| DD (%/drug/insp. filter) ± SD | 53.2% | 53.4 ± 1.4% | 53.9% |
| DDR (mg drug/min) | 22.1 | 22.5 | 24.4 |
| FF (droplets <5.8 μm) measured by LD | 82.0% | 82.0% | 82.0% |
| RD (mg drug) | 40.4 | 81.2 | 122.6 |
| RDDR (mg drug/min) | 18.3 | 18.6 | 20.2 |
| Nebulization time (min) | 2.21 | 4.37 ± 0.60 | 6.09 |

IMP = improved with a vibrating perforated membrane.

In Table 7, the PARI eFlow nebulizer was used to determine the efficacy of the drug delivery. The study was designed to compare nebulization of the nominal drug dose, 92 mg in 1, 184 mg in 2 ml and 276 mg in 3 mL of the solvent. Both delivered dose (DD) and respirable dose (RD) are expressed in mg of drug. Additionally, the drug (mg) delivered per 1 minute (DDR and RDDR) and nebulization were determined. Results seen in the nebulization time column shows that respirable dose 40.4 mg can be delivered in 2.21 minutes, 81.2 mg can be delivered in 4.37 minutes and 122.6 mg of the drug can be delivered by 6 minutes long nebulization.

Results seen in Table 7 clearly show that the use of the PARI eFlow electronic nebulizer results in a significant improvement of the drug delivery rate and that the time of the drug delivery can be substantially shortened while the efficacy of the delivery is not affected by such time shortening.

B. Dry Powder Inhalers

Dry powder is administered as such using devices such as dry powder or meter dose inhalers which deliver the dry powder directly to the lungs.

For use in dry powder inhalers, the lidocaine or a lidocaine-like compound is formulated as a dry powder, as described above, in dosages from 1-100 mg, preferably from 10-50 mg. The particle sizes of the powder are such that when the powder is emitted from the inhaler, it forms an aerosol with a mass median diameter of between about 3.5-10 am, preferably substantially between 4 μm and about 5 μm.

C. Efficacy of Lidocaine or a Lidocaine-Like Compound Nebulization

As described above, the selection and choice of the nebulizer greatly affects efficacy of the delivery of the inhalable lidocaine or a lidocaine-like compound.

A combination of an aerosol formulation of lidocaine or a lidocaine-like compound and a nebulizing device significantly enhances the efficiency and speed of lidocaine or a lidocaine-like compound administration.

Currently, for example the average time for administration of inhaled lidocaine or a lidocaine-like compound solutions using other formulations and nebulizers is 10-20 minutes per dose. Since, at this time, no safe and convenient plastic vial for packaging and storage of the lidocaine solution is available, patients need to use glass vials of i.v. lidocaine, assure that there are no preservatives in the formulation, extract a defined amount of lidocaine from the vial by use of a syringe, and inhale via jet nebulizer. Such inhalation typically requires at least 10-20 minutes.

The time required for the currently available treatments results a significant loss of the drug, loss of the time, places unnecessary burden on the patient and contributes to reduced compliance with the daily regimen.

Furthermore, the nebulizer systems used previously for lidocaine administration are less efficient than new electronic devices. Using these nebulizers, the total deposited dose of drug in the lung is in the 12 to 15% range, at maximum. Approximately 30% of the dispensed drug remains in the nebulizer at the end of treatment, and of the portion that is aerosolized, about 30% is emitted as particles too large or too small to reach the central airways. Oropharyngeal numbing, impairment of the gag reflex, cough, shortness of breath and breathlessness caused by a deposition of the drug in the peripheral and/or upper lungs and other systemic side effects are the consequences of these treatments.

The novel electronic nebulizer, with an output of 8 to 10 microliters/seconds, or 0.48 to 0.60 ml/minute, is capable of delivering drug material 2 to 30 times faster than the prior nebulizers. Furthermore, the novel nebulizer is able to aerosolize more than 90% of the dispensed dose. As a result, administration of a specifically designed formulation of lidocaine or a lidocaine-like compound using the electronic nebulizer leads to substantial improvement in delivery of the drug to the central airways, in a shorter time required for delivery and, depending on the final concentration of lidocaine or a lidocaine-like compound in the inhalable solution, reduces treatment time to as little as one to two minutes.

VI. Treatment of Cough and Tussive Attacks and Episodes

The method of the invention provides for efficacious treatment of cough, tussive attacks and episodes.

A. Treatment of Cough

Aerosol therapy of this invention is particularly useful for treatment of patients suffering from cough, tussive attacks and episodes of all origins. Additionally, the therapy is useful for abatement of cough accompanying pulmonary diseases and is especially suitable for treatment of patients with intractable cough, after exclusion of lung cancer and other possibly fatal diagnoses. Cough may also be treated specifically with inhaled lidocaine, along with other causal treatments for the underlying disease that occurs with cough, such as asthma, chronic obstructive pulmonary disease (COPD), lung neoplasia, cystic fibrosis, chronic bronchitis, gastroesophageal reflux, sarcoidosis, etc.

There are also numerous patients with chronic cough after a viral infection of the upper airways, i.e. post infectious cough, who will benefit from the treatment of the current invention.

In addition, it has been observed that cough patients with increased sensitivity to environmental airway challenges from smoke, dust, and airway pollution show have substantial improvement of their symptoms when treated with 10 mg or 40 mg inhaled lidocaine twice daily using the method of the invention.

It has also been discovered that inhalable lidocaine provides successful treatment for cough appearing in patients with cystic fibrosis, bronchiectasis or other suppurative pulmonary disease.

Treatment of these conditions with aerosolized lidocaine has been successful in suppressing the cough.

B. Advantages of Inhalable Lidocaine

Lidocaine possesses several features that make it very attractive for administration to patients.

The first of these features stems from its mechanism of action, which involves modulation of nerve conductivity, and control of smooth muscle of airways by inhibition of uptake transporters and numbing.

Medically, the advantages of the current invention are substantially improved safety, tolerability, and targeted dosing with the eFlow.

VII. In Vivo Testing

The conditions requiring particular attention are cough and tussive attacks occurring during or accompanying asthma.

In order to determine if an appropriately formulated lidocaine for aerosolization could become effective for treatment of severe and persistent cough, the treatment with aerosolized lidocaine was initiated and tested in asthmatic patients experiencing cough. The clinical treatment and results obtained with an aerosolized lidocaine is described in Example 4.

UTILITY

The method of the invention is suitable for treatment of cough and tussive attacks or episodes. The inhalable lidocaine compositions disclosed herein provide efficacious means for management of cough regardless of the cough origin and is suitable for treatment of severe and persistent cough such as occurring in cold, flu, cough or hacking cough.

EXAMPLE 1

Lidocaine or a Lidocaine-Like Compound Solution for Inhalation

This example describes the preparation of a solution for inhalation comprising lidocaine or a lidocaine-like compound used for in vivo studies.

Lidocaine solution for inhalation (LSI) is provided as a 1.0 mL sterile, preservative free, nonpyrogenic single dose ampule. The ampules contain 10 or 40 mg of lidocaine hydrochloride, USP (1 mL of 1% or 4% of lidocaine), in a pH range of 5.0 to 7.0. The added sodium chloride content is 6.844 g/L of sodium chloride USP for 1% lidocaine, and 0.351 g/L of sodium chloride USP for 4% lidocaine. The osmolality for both solutions is approximately 275-300 mOsm/kg.

LSI is intended for use in combination with the PARI eFlow nebulizer.

Preparation of the inhalable solution comprising lidocaine-like compounds follows the same preparation protocol.

EXAMPLE 2

Preparation of Dry Powder Comprising Lidocaine or a Lidocaine-Like Compound

This example provides methods and procedures used for preparation of lidocaine or a lidocaine-like compound containing inhalable dry powder.

For dry powder formulation of the invention, a purified lidocaine or a lidocaine-like compound is processed to a powder having mass median average diameters ranging from 3 μm to 10 μm by media milling, jet milling, spray drying, or particle precipitation techniques.

Media milling may be accomplished by placing lidocaine or a lidocaine-like compound substance into a mill containing, for example, stainless steel or ceramic balls and rotating or tumbling the material until the desired drug particle size ranges are achieved.

Jet milling uses very high pressure air streams to collide particles with one another, with fine particles of the desired size being recovered from the mill.

Spray drying is achieved by spraying a fine mist of lidocaine or a lidocaine-like compound solution onto a support and drying the particles. The particles are then collected.

Particle precipitation is achieved by adding a co-solvent to spray dried particles. The solubility of the drug falls to the point where solid drug particles are formed. The particles are collected by filtration through 3 µm filter or centrifugation. Precipitation has the advantage of being highly reproducible and can be performed under low temperature conditions, which reduce degradation.

Other technologies available to be used for preparation of dry powders may also be used.

EXAMPLE 3

Dry Powder Inhalers for Use with Lidocaine or a Lidocaine-Like Compound Powder

The lidocaine or a lidocaine-like compound dry powder formulations of the invention may be used directly in metered dose or dry powder inhalers.

A metered dose inhaler consists of three components: a canister containing the propellant lidocaine or a lidocaine-like compound suspension, a metering valve designed to deliver accurately metered volumes of the propellant suspension, and an oral adapter which contains a spray orifice from which the metered dose is delivered. In the rest position, the metering chamber of the valve is connected to the drug suspension reservoir via a filling groove or orifice. On depression of the valve this filling groove is sealed and the metering chamber is exposed to atmospheric pressure via the spray orifice in the oral adapter and the valve stem orifice. This rapid pressure reduction leads to flash boiling of the propellant and expulsion of the rapidly expanding mixture from the metering chamber. The liquid/vapor mixture then enters the expansion chamber which is constituted by the internal volume of the valve stem and the oral adapter. The mixture undergoes further expansion before being expelled, under its own pressure, from the spray nozzle. On exit from the spray orifice, the liquid ligaments which are embedded in propellant vapor are torn apart by aerodynamic forces. Typically, at this stage, the droplets are 20 to 30 µm in diameter and are moving at the velocity of sound of the two-phase vapor liquid mixture (approximately 30 meters per second). As the cloud of droplets moves away from the spray nozzle, it entrains air from the surroundings and decelerates, while the propellant evaporates through evaporation, the entrained droplets eventually reach their residual diameter.

At this point, the particles/droplets consist of a powdered lidocaine or a lidocaine-like compound core coated with surfactant. Depending on the concentration and the size of the suspended material the powdered drug core consists of either individual drug particles or aggregates.

An alternated route of lidocaine or a lidocaine-like compound dry powder delivery is by dry powder inhalers.

Excipients commonly used for dry powder formulations are lactose, however in the case of lidocaine or a lidocaine-like compound free base, the addition of the amino acids lysine or leucine will lead to better powder formation.

Effective dosage levels of lidocaine or a lidocaine-like compound for dry powder inhalation and metered dose inhalation result in the application of a nominal dose of at least about 10 mg, and more preferable about 40 mg of lidocaine or a lidocaine-like compound to the conducting and central airways of the patient receiving treatment. Deposited dose are 2 and 20 mg in the conducting and central airways for 10 mg and 40 mg nominal dose, respectively. Depending on the efficiency of the dry powder delivery device, dry powder formulations suitable for use in the invention comprise from about 1.0 to about 50 mg, preferably from about 10 to about 40 mg of powder in an amorphous or crystalline lidocaine or a lidocaine-like compound in particle sizes between 3 μm and 10 μm in mass median average diameter necessary for efficacious delivery of lidocaine or a lidocaine-like compound into the central airways. The dry powder formulation is typically delivered in conjunction with the delivery of the primary drug a and may occur 1 to 4 times daily. The dry powder formulations are temperature stable and have a physiologically acceptable pH of 5.0 to 7.5, preferably 5.5 to 7.0, and long shelf lives.

EXAMPLE 4

Lidocaine Solution for Inhalation Used for Treatment of Asthma Patients

This example describes a clinical trial with inhalable lidocaine (10 and 40 mg) for treatment of asthma patients, some of whom were also treated with albuterol.

The clinical trial was performed in a double blinded, placebo controlled study in mild to moderate asthma patients. For the study, 10 mg (1 ml of 1% lidocaine/saline), 40 mg (1 ml of 4% lidocaine/saline) of lidocaine solution for inhalation or placebo (1 ml of saline) was administered by the electronic nebulizer PARI eFlow, modified. The lidocaine solution was administered either alone or in conjunction with administration of albuterol twice daily.

Asthma patients (100 females and 54 males, 31.3±1.8 years of age, $FEV_1$, 78.4±1.8% predicted) were enrolled, randomized to three groups, and treated for 12 weeks. The full individual doses of 1 ml were administered in 2-3 minutes treatment time.

Both doses of lidocaine were found to be well tolerated and safe, and no difference was found in the number of patients with at least one adverse events (AEs) were found between placebo (30/48, 63%), 10 mg lidocaine (39/55, 71%), and 40 mg lidocaine (33/51, 65%). Particularly, there was no difference in the number of patients with one or more respiratory AEs between placebo (14/48, 29%), 10 mg lidocaine or a lidocaine-like compound (16/55, 29%), and 40 mg lidocaine or a lidocaine-like compound (18/51, 35%).

Airway irritation and acute bronchospasm were assessed by measuring spirometry immediately prior to and 30 min post-completion of aerosol administration. A decrease in forced expired volume in one second (FEV1)>20% in the 30 minutes spirometry test was considered evidence of bronchospasm. All patients were tested for bronchospasm upon aerosolization of all three doses mentioned above (LSI 1%, 4%, and placebo), and FEV1 was compared before and after drug application of drug. None of the 154 treated had occurrence of bronchospasm.

The amount of complaints about oropharyngeal numbing was greatly reduced when compared to previous studies with inhaled lidocaine given by other nebulizers. Numbing in all previous studies had been noted in virtually all subjects, whereas the incidence of numbing in this clinical trial was 40% (22/55) and 31.45% (16/51) of treated patients, noted at least once during the course of the 12 week study and 60% in 1% group and 68.6% in 4% group of lidocaine treated patients did not have any complaints of numbing at all.

No loss of gag reflex was reported. No case of tracheal aspiration of food or liquid was reported. Most importantly, there were no reports of bronchospasm upon lidocaine delivery, nor was there any report of a clinically significant $FEV_1$ drop upon lidocaine inhalation (the measure for bronchospasm).

Within the Asthma Quality of Life Questionnaires (AQLQ) (environmental domain), all patients were asked about how they tolerated impact of dust, smoke, and air pollution. When AQLQs were analyzed, a significant improvement was observed at week 12 from the baseline between treatment groups and placebo in the environmental domain of the questions (mean changes were placebo=0.35; 10 mg lidocaine=2.09; and 40 mg lidocaine=2.45; p=0.012 for 10 mg lidocaine v. placebo, p=0.01 for 40 mg v. placebo).

These results indicate a post-treatment improvement of airway susceptibility and asthma in tolerating environmental airway challenges like smoke, dust, pollution, allergens, etc. The lung deposition of lidocaine is increased two- to three-fold. The same efficacious amount can be delivered in ⅓ of the time used previously. The safety profile is greatly improved, with abolished bronchospasm, greatly reduced incidence of oropharyngeal numbing, loss of gag reflex with lower lung and systemic deposition of lidocaine.

These results confirm that the inhalable lidocaine or a lidocaine-like compound administered according to the invention is safe and tolerable upon its delivery to the conducting airways. None of the descriptions of prior art provided a convenient, tolerable and safe administration of lidocaine or a lidocaine-like compound to the upper and central airways.

EXAMPLE 5

Clinical Case

This example describes a clinical study for treatment of cough using 1% of lidocaine.

A 38 year old, otherwise healthy male patient had experienced postnasal drip and persistent cough for two weeks, after having had an upper respiratory infection. Cough episodes were occurring hourly during the day, and were influencing the patients' sleep at night.

2.5 ml of lidocaine 1% (25 mg) were administered as a single dose via PARI eFlow nebulizer generating an aerosol with MMAD between 3 and 10 μm. During and shortly after the treatment (which was approximately 10 min in duration), no significant numbing of the oropharynx nor loss of gag reflex was reported, and only a transient numbing of the tongue was noted. Also, the patient reported good tolerability, and no otherwise untoward effects. After this single treatment, the patients' cough was greatly diminished over the course of the following day, and the patient remained essentially free of cough for the following two weeks. The patient was not followed up any further.

What is claimed is:

1. A method for treatment of cough, tussive attacks or tussive episodes by a targeted delivery of a local anesthetic to trachea, carina, and bronchi of a patient in need thereof without co-administering a bronchodilator, said method comprising steps:
    a) preparing an inhalable dry powder consisting essentially of about 10 to about 80 mg of said local anesthetic selected from the group consisting of proparacaine, cocaine, procaine, tetracaine, hexylcaine, bupivacaine, lidocaine, benoxinate, mepivacaine, prilocalne, mexiletene, vadocaine and etidocaine; and an excipient selected from the group consisting of lactose, lysine and leucine;
    b) selecting dry powder inhaler or meter dose inhaler able to generate aerosol of particle sizes substantially between 3.0 and 10 μm;
    c) nebulizing said inhalable dry powder into an aerosol, wherein at least 80% of the particles have a mass median aerodynamic diameter between about 3 and 10 μm and a geometric standard deviation lower than 1.7; and
    d) administering said aerosol to said patient once, twice or several times a day; wherein said administration results in deposition of said local anesthetic in trachea, carina, and bronchi for treatment of cough or tussive attacks or episodes; without cousin bronchospasm loss of gag reflex, oropharyngeal numbing, or systemic circulation of said local anesthetic.

2. The method of claim 1 wherein said local anesthetic is lidocaine.

3. The method of claim 2 wherein said lidocaine dry powder is delivered by the dry powder inhaler one to four times a day as a dry powder aerosol, wherein at least 90% of the particles have sizes between 3.5 and 5 μm.

4. The method of claim 2 wherein said lidocaine dry powder is delivered by the metered dose inhaler one to four times a day as a dry powder aerosol of particles, wherein at least 90% of the particles have sizes between 3.5 and 5 μm.

5. The method of claim 1 used for treatment of a patient suffering from cough or from tussive attacks or episodes resulting from asthma, chronic obstructive pulmonary disease, cystic fibrosis, lung cancer, lung neoplasia, chronic bronchitis, bronchiectasis, suppurative pulmonary disease, gastroesophageal reflux, sarcoidosis or acute or chronic cough resulting or connected with a viral or bacterial infection of the upper airways.

6. An inhalable dry powder composition for treatment of cough, tussive attacks and tussive episodes for a targeted delivery of said inhalable dry powder into trachea, carina, and bronchi of a patient in need thereof without co-administering a bronchodilator, said composition consisting essentially of from about 10 to about 80 mg of a local anesthetic selected from the group consisting of proparacaine, cocaine, procaine, tetracaine, hexylcaine, bupivacaine, lidocaine, benoxinate, mepivacaine, prilocalne, mexiletene, vadocaine and etidocaine wherein said dry powder has a particle size with a mass median aerodynamic diameter from about 3 μm to about 10 μm; and an excipient selected from the group consisting of lactose, lysine and leucine.

7. The composition of claim 6 wherein said local anesthetic is lidocaine.

8. The composition of claim 7 wherein said dry powder is milled, spray dried, lyophilized or particle precipitated.

9. A method for treatment of cough, tussive attacks or tussive episodes by a targeted delivery of lidocaine dry powder in trachea, carina, and bronchi of a patient in need thereof without co-administration of bronchodilator, said method comprising administering to a subject in need thereof from about 10 mg to about 80 mg lidocaine formulated as a dry powder and delivered by a dry powder or metered dose inhaler that produces an aerosol with a mass median diameter between about 3 and about 10 with a geometric standard deviation smaller than 1.7,
    wherein an oropharyngeal deposition of said lidocaine is smaller then 10%;
    wherein said dry powder or meter dose inhaler deposits at least 25% of the total drug in the central conducting airways;
    wherein said treatment is administered once, twice or several times a day.

10. The method of claim 9, wherein the cough is intractable cough, resulting from or connected with another underlying disease.

11. The method of claim 10, wherein the underlying disease is asthma, chronic obstructive pulmonary disease, lung neoplasia, cystic fibrosis, chronic bronchitis, bronchiectasis, suppurative pulmonary disease, gastroesophageal reflux, sarcoidosis, acute or chronic cough resulting from or connected with a viral or bacterial infection of the upper airways.

12. The method of claim 11, wherein the underlying disease is aggravated or wherein a patient suffering from the underlying disease experiences increased sensitivity to environmental airway challenges from smoke, smog, dust, allergies or air pollution.

13. A method for treatment of cough or tussive attacks or tussive episodes connected with environmental challenges due to smoke, smog, air pollution, dust or allergens, by a target delivery of a local anesthetic to trachea, carina, and bronchi of a patient in need thereof without co-administrating a bronchodilator, said method comprising steps:
 a) preparing an inhalable dry powder consisting essentially of about 10 mg or about 40 mg of lidocaine; and an excipient selected from the group consisting of lactose, lysine and leucine;
 b) selecting a dry powder or meter dose inhaler;
 c) nebulizing said inhalable lidocaine dry powder into an aerosol, wherein at least 80% of the particles have a mass median aerodynamic diameter between about 3 μm and about 10 μm and a geometric standard deviation lower than 1.7; and
 d) administering said aerosol to the patient exposed to or following exposure to smoke, smog, air pollution, dust or allergens, immediately before or immediately after the exposure; wherein said administration results in deposition of said inhalable lidocaine dry powder in trachea, carina, and bronchi for treatment of cough or tussive attacks or tussive episodes; without causing bronchospasm, loss of gag reflex, oropharyngeal numbing or systemic circulation of lidocaine.

* * * * *